(12) United States Patent
Chen et al.

(10) Patent No.: US 11,179,158 B2
(45) Date of Patent: Nov. 23, 2021

(54) HANDLE ASSEMBLY AND STAPLER INCLUDING THE SAME

(71) Applicant: TOUCHSTONE INTERNATIONAL MEDICAL SCIENCE CO., LTD., Jiangsu (CN)

(72) Inventors: Zhi Chen, Jiangsu (CN); Yi Guo, Jiangsu (CN); Jiang Lin, Jiangsu (CN); Xiaowei Xu, Jiangsu (CN)

(73) Assignee: Touchstone International Medical Science Co., Ltd.

( * ) Notice: Subject to any disclaimer, the term of this patent is extended or adjusted under 35 U.S.C. 154(b) by 0 days.

(21) Appl. No.: 16/957,533

(22) PCT Filed: Nov. 29, 2018

(86) PCT No.: PCT/CN2018/118111
§ 371 (c)(1),
(2) Date: Jun. 24, 2020

(87) PCT Pub. No.: WO2019/128607
PCT Pub. Date: Jul. 4, 2019

(65) Prior Publication Data
US 2021/0059678 A1    Mar. 4, 2021

(30) Foreign Application Priority Data

Dec. 26, 2017    (CN) .......................... 201721849649.6

(51) Int. Cl.
*A61B 17/064* (2006.01)
*A61B 17/115* (2006.01)
(Continued)

(52) U.S. Cl.
CPC ......... *A61B 17/1155* (2013.01); *A61B 17/326* (2013.01); *A61B 2017/00367* (2013.01);
(Continued)

(58) Field of Classification Search
CPC ...... A61B 17/1155; A61B 2017/00367; A61B 2017/2925
See application file for complete search history.

(56) References Cited

U.S. PATENT DOCUMENTS

| 4,351,466 A * | 9/1982 | Noiles ................. A61B 17/115 227/8 |
| 7,658,311 B2 * | 2/2010 | Boudreaux ...... A61B 17/07207 227/175.2 |

(Continued)

FOREIGN PATENT DOCUMENTS

| CN | 106344095 A | 1/2017 |
| CN | 206403834 U | 1/2017 |

(Continued)

OTHER PUBLICATIONS

International Search Report regarding PCT/CN2018/11811; dated Feb. 13, 2019.
(Continued)

*Primary Examiner* — Eyamindae C Jallow
(74) *Attorney, Agent, or Firm* — Dickinson Wright PLLC

(57) ABSTRACT

A handle assembly and a surgical stapler including the handle assembly is provided, wherein the handle assembly includes a first handle and a second handle. A first limit portion and a second limit portion are provided on one end of the first handle and one end of the second handle, respectively. The first limit portion is on a proximal end side of the second limit portion. As the first handle is at its initial position, the first limit portion abuts the second limit portion to prevent the first handle from rotation in a second direction. In an invalid state, the first handle can still be squeezed; meanwhile, the first and the second limit portions limit the initial angular position of the first handle and the initial position of the second handle. When the first handle is not (Continued)

rotated, the second handle cannot be rotated and the stapler cannot be fired.

10 Claims, 15 Drawing Sheets

(51) Int. Cl.
    *A61B 17/326* (2006.01)
    *A61B 17/00* (2006.01)
    *A61B 17/072* (2006.01)

(52) U.S. Cl.
    CPC ............ *A61B 2017/07257* (2013.01); *A61B 2017/07271* (2013.01); *A61B 2017/07285* (2013.01)

(56) References Cited

U.S. PATENT DOCUMENTS

| | | | |
|---|---|---|---|
| 7,770,775 B2* | 8/2010 | Shelton, IV | A61B 34/76 227/178.1 |
| 9,445,810 B2* | 9/2016 | Cappola | A61B 17/068 |
| 9,549,738 B2* | 1/2017 | Mandakolathur Vasudevan | A61B 17/072 |
| 9,603,599 B2* | 3/2017 | Miller | A61B 17/115 |
| 2005/0103819 A1* | 5/2005 | Racenet | A61B 17/068 227/175.1 |
| 2010/0301098 A1 | 12/2010 | Kostrzewski | |
| 2011/0006100 A1 | 1/2011 | Milliam | |
| 2013/0175320 A1 | 7/2013 | Mandakolathur Vasudevan | |
| 2014/0263548 A1* | 9/2014 | Tanner | A61B 17/1155 227/175.2 |

FOREIGN PATENT DOCUMENTS

| | | |
|---|---|---|
| CN | 106388948 A | 2/2017 |
| CN | 106456166 A | 2/2017 |
| CN | 206261635 U | 6/2017 |
| CN | 107485429 A | 12/2017 |
| JP | 2009189831 A | 8/2009 |
| JP | 2015503949 A | 2/2015 |
| RU | 2025093 C1 | 12/1994 |

OTHER PUBLICATIONS

Communication regarding corresponding RU Pat. App. 2020122857/14; dated Nov. 20, 2020.
Examination Report No. 1 regarding corresponding AU App. No. 2018396724; dated Oct. 20, 2020.
English Translation of Office Action regarding corresponding JP App. No. 2020-535122; dated Jun. 17, 2021.
Extended European Search Report regarding corresponding EP App. No. 18897799.5, dated Aug. 16, 2021.

* cited by examiner

HANDLE ASSEMBLY AND STAPLER INCLUDING THE SAME

CROSS-REFERENCE TO RELATED APPLICATIONS

This application is based upon PCT patent application No. PCT/CN2018/118,111, filed on Nov. 29, 2018, which claims priority to Chinese Patent Application No. 201721849649.6, filed on Dec. 26, 2017, the entire contents of which are incorporated herein by reference.

TECHNICAL FIELD

The present disclosure relates generally to surgical instruments, more particularly, to stapler technology, and specifically to a handle assembly and a stapler comprising the same handle assembly.

BACKGROUND

Digestive tract tumor is one of human diseases of high incidence. During treatment a circular stapler is widely used for suturing physiological tissues such as tissues in the digestive tract, replacing the manual operation by doctors. The circular stapler is a surgical instrument commonly used in suturing remaining end sections, in either end to end or end to side manner, of the physiological tissues of esophagus, stomach, intestine, etc., in a way of axial internal stapling. During the process of anastomoses, two sections of tissues are accommodated in the stapler, and form a circular anastomotic stoma after firing the stapler, to rebuild a tissue channel.

In the prior art, the circular stapler includes a body portion, a handle assembly detachably connected to the body portion and an anvil assembly matched with the body portion. The body portion includes a cartridge assembly positioned on a distal end which includes a cylindrical cartridge and a knife, and a knob positioned on a proximal end, thereof, which can be rotated relative to the body portion. In the present disclosure, the positions of the distal end and the proximal end are defined relative to an operator, wherein, the proximal end is a closest end to the operator and the distal end is a furthest end from the operator and closest to a surgical site. The anvil assembly includes an anvil, an anvil head on the top of the anvil, a cutter inside the anvil and an anvil shaft detachably connected to the body portion. In surgical operation, after the tumor tissues are separated and cored, the anvil shaft is connected to the distal end of instrument body through a purse on one end of the tissues; the knob is rotated to shorten a distance between the cartridge and the anvil to an appropriate distance when the stapler can be fired in performing the suturing. As the development of surgical instruments advances, circular staplers have been more widely used for treatment of diseases such as hemorrhoids.

Meanwhile, in urinary surgical field, another kind of circular stapler is also applied to treat redundant prepuce and phimosis, which is called circumcision stapler. The structure of the circumcision stapler is similar to the circular stapler for digestive tract as aforementioned, except for the glans cap assembly configured to work with the body portion. Similarly, the glans cap assembly includes an anvil, a glans cap fixedly connected to the anvil, a cutter anvil and a central rod detachably connected to the body portion. During operation, the prepuce tissues to be removed are fixed to the glans cap, the central rod is disposed at the distal end of the body portion, and the knob is rotated to shorten a distance between the glans gap and the cartridge assembly to an appropriate distance. The stapler is then able to be fired by squeezing the handle to accomplish the anastomosis.

Along with the technological development, the firing mechanism of the circular stapler has been improved with an added a lockout mechanism. When the stapler is not ready to be fired, even squeezing the handle wouldn't actuate the handle, thus prevent the stapler from being fired by mistake. However, in practice, the lockout mechanism has some defects. For example, the insurance mechanism affects negatively on the operators' experience, and the housing of the stapler may be ruptured if the operator squeezes the handle with excessive force.

In addition, an initial angle exists between the handle and the housing of the stapler. While firing the stapler, the operator squeezes the handle to decrease the angle until the handle is close to the housing of the stapler. However, the existing handle lacks a limiting structural design, leaving an excessively large opening angle at the initial position, which causes inconvenience to the operator.

SUMMARY

In relation to the problems in the prior art, the objective of the present disclosure is to provide a handle assembly and a stapler including the handle assembly. Such handle assembly limits an angular deflection of a first handle at an initial position, improves installation accuracy of the first handle, and limits an initial position of a second handle.

The present disclosure provides a handle assembly for firing a stapler, including:

a first handle and a second handle, wherein one end of the first handle is rotatably attached to one end of the second handle;

when the first and the second handle are not linked, the second handle is in an insurance position; when the first handle and the second handle are linked, the rotation of the first handle in a first direction moves the second handle from the insurance position to a firing position;

the first handle is provided, on its one end, with a first limit portion; and the second handle is provided, on its one end, with a second limit portion; the first limit portion is located on a proximal end side of the second limit portion; when the first handle is in an initial position, the second limit portion engages the first limit portion to block rotation of the first handle in a second direction.

In some embodiments of the present disclosure, the first direction is counterclockwise, and the second direction is clockwise; or, the first direction is clockwise, the second direction is counterclockwise.

In some embodiments of the present disclosure, the first handle includes a first cavity, the first limit portion is a limit pivot pin located inside the first cavity, and two ends of the limit pivot pin are fixed to two side walls of the first cavity respectively;

when the first handle is in the initial position, a side surface of the limit pivot pin abuts the second limit portion.

In some embodiments of the present disclosure, the second limit portion includes two limiting posts, with an imaginary line connecting thereto parallel to a central axis of the limit pivot pin;

when the first handle is in the initial position, the limit pivot pin simultaneously abuts both limiting posts.

In some embodiments of the present disclosure, wherein the second handle is provided with a second cavity, and the second limit portion comprises two limiting posts which are respectively located on lower parts of side walls of the second cavity;

when the first handle is in the initial position, the first limit portion simultaneously abuts both limiting posts.

In some embodiments of the present disclosure, the limiting posts and the side walls of the second cavity are integrally formed.

In some embodiments of the present disclosure, the first handle is provided with a sliding slot which comprises two interconnected sections: a first section and a second section; a slider is slidably disposed in the sliding slot;

when the slider is located in the first section of the sliding slot, as the first handle is rotated in the first direction, the slider does not engage the second handle, thus the first handle and the second handle are not linked; when the slider is located in the second section of the sliding slot, as the first handle is rotated in the first direction, the slider abuts the second handle and pushes the second handle to rotate with the first handle.

In some embodiments of the present disclosure, the handle assembly further includes:

an indicator attached to a distal end of a pulling sheet, a proximal end of which is sleeved on a screw rod;

a knob provided at a distal end of the screw rod, and when the knob is rotated, the pulling sheet is moved thereby towards a proximal end of the stapler;

the pulling sheet moves the indicator from a first position area to a second position area, while pushing the slider from the first section to the second section of the sliding slot.

In some embodiments of the present disclosure, the handle assembly further includes:

a first pivot pin, passing through the first handle and the second handle, is fixed to a housing of the stapler;

a first torsion spring sleeved on the first pivot pin, and two ends thereof abut the housing of the stapler and the second handle, respectively;

a second pivot pin fixed to the housing of the stapler;

a second torsion spring sleeved on the second pivot pin, and two ends of the second torsion spring respectively abut the housing of the stapler and the first handle.

The present disclosure further provides a stapler, including the handle assembly.

The handle assembly and the stapler including the handle assembly provided by the present disclosure have the following advantages:

The present disclosure provides a handle assembly and a stapler including the handle assembly. The handle assembly includes a first handle and a second handle which can be configured different linkage states, and only the rotation of the second handle can fire the stapler, thereby avoiding accidental firing. In an invalid state, the first handle can still be squeezed without causing rupture of the housing. The first handle is provided with a first limit portion and the second handle is provided with a second limit portion. In an initial state, the two limit portions abut each other to prevent the rotation of the first handle in a second direction, so that the angular deflection of the first handle in its initial position will not be too great, ensuring high accuracy of the initial position of the first handle and improving the operator's experience; in addition, the two limit portions limit the initial position of the second handle so that when the first handle is not rotated, the second handle cannot be rotated to fire the stapler.

BRIEF DESCRIPTION OF THE DRAWINGS

Various detailed non-limiting embodiments of the present disclosure are described herein, with references to the drawings, to elaborate on features, objectives, and advantages.

DETAILED DESCRIPTION

In the following, embodiments of the present disclosure will be described in details with reference to the drawings. The concept of the present disclosure can be implemented in a plurality of forms, and should not be understood to be limiting. In contrary, these embodiments are provided to make the present disclosure more comprehensible and understandable, and so the conception of the embodiments can be conveyed to those skilled in the art fully. Reference marks in the figures refer to same or similar elements, so repeated description of them will be omitted.

Figure 1:
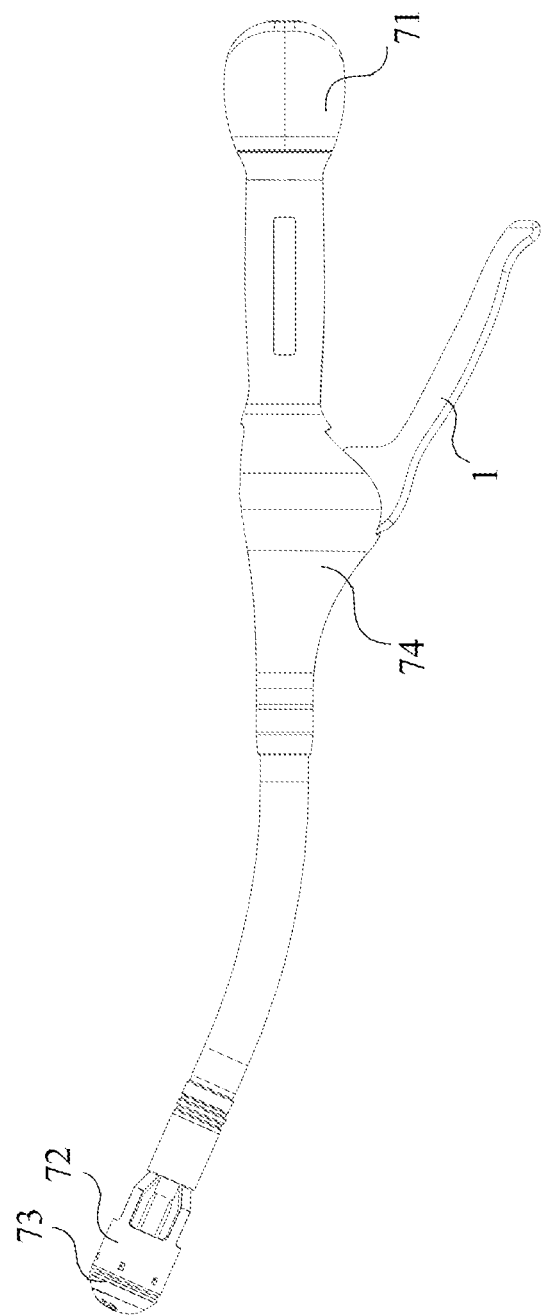
FIG. 1 is a schematic view of a handle assembly according to an embodiment of the present disclosure applied in a stapler.
Figure 2:
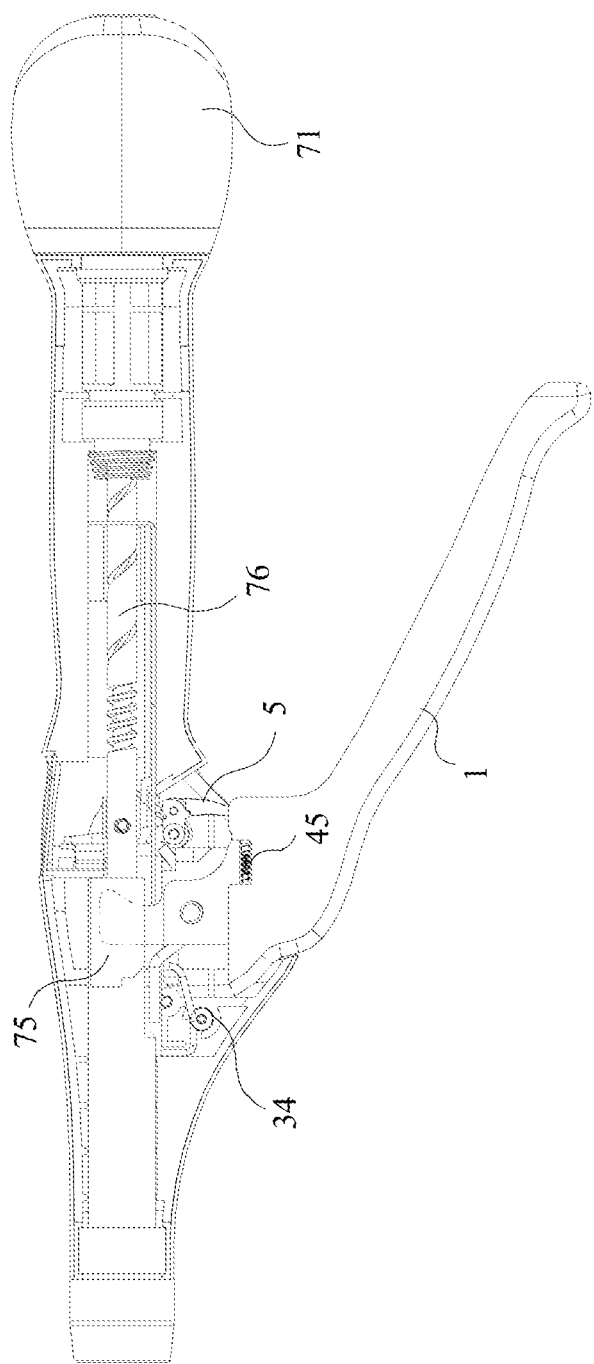
FIG. 2 is a schematic view of the handle assembly according to the embodiment of the present disclosure applied in a regular stapler.

FIG. 1 shows the structure of the stapler according to an embodiment of the present disclosure, wherein a staple cartridge assembly 72 and an anvil assembly 73 are provided at a distal end of the stapler, a knob 71 and a handle assembly are provided at a proximal end of the stapler. The stapler can be fired by actuating the handle assembly.

FIGS. 2-7 show the structure of the handle assembly in an initial position according to the embodiment of the present disclosure. In order to clearly show the structure and mechanism of the handle assembly and the other parts, partial housing and components have been omitted in the figures. The handle assembly according to the present disclosure provides a first handle 1 and a second handle 2. Only when the second handle 2 is rotated can the stapler be fired. One end of the first handle 1 and one end of the second handle 2 are pivotally attached. When the first handle 1 and the second handle 2 are not linked, as the operator squeezes the first handle 1, the second handle 2 cannot be rotated, thus the stapler cannot be fired. When the first handle 1 and the second handle 2 are linked, the operator squeezing the first handle 1 causes the second handle 2 to rotate, thereby firing the stapler.

To control the linkage state of the first handle 1 and the second handle 2, the first handle 1 is further provided with a sliding slot 41 and a slider 42. The sliding slot 41 includes a first section and a second section connected with each other. The second handle 2 includes a handle abutment 25; when the slider 42 is positioned in the first section of the sliding slot 41, as the first handle 1 is rotated in a first direction, the slider 42 does not engage the handle abutment 25. As such the second handle 2 is in an insurance position. That is to say, although the first handle 1 is rotated, the handle assembly is in an invalid state, therefore the stapler cannot be fired. In this embodiment, the first direction is a counterclockwise direction shown in the figure, but the present disclosure is not limited to this configuration. Therefore, when an operator squeezes, the first handle 1 can be easily rotated, but the second handle 2 is not actuated. As the stapler is not being fired, the force required to rotate the first handle 1 is very mall. The operator can immediately learn that the stapler is not fired, and will not apply excessive force that may ruptures the stapler housing.

When the slider 42 is positioned in the second section of the sliding slot 41, and the first handle 1 is rotated in the counterclockwise direction, the slider 42 engages the handle abutment 25 and rotates the second handle 2 from the insurance position to a firing position. When the second handle 2 is rotated in the counterclockwise direction, it simultaneously advances a staple pushing rod 75 distally, thereby fires the stapler.

It should be noted that the first section and the second section of the sliding slot 41 in the present disclosure are relative terms, i.e. not necessarily referred to two ends of the sliding slot 41. As shown from the perspectives in the FIG. 5, the first section of the sliding slot 41 is positioned on the right side of the second section. When the slider 42 is positioned in the first section of the slide slot 41, it will not engage the handle abutment 25, whereas in the second section of the slide slot 41, it will engage the handle abutment 25.

In the embodiment of the present disclosure, the movement of the slider 42 from the first section to the second section of the sliding slot 41 is adjusted by an indicator 5. The indicator 5 includes a first end 51, a positioning portion 53 and a second end 52. The first end 51 of the indicator 5 is provided with a protrusion 54 which is located correspondingly to a position of a hook of a pulling sheet 6. The positioning portion 53 of the indicator 5 is pivotally attached to the housing 74 of the stapler. A tail of the pulling sheet 6 is fixed to a screw rod 76 and will move along the screw rod 76. When the knob 71 is rotated in one direction, the screw rod 76 will move towards the proximal end of the stapler, advancing the pulling sheet 6 proximally. The hook of the pulling sheet 6 may then effect a movement of the first end 51 of the indicator 5 in the second direction, so that when the first end 51 of the indicator 5 moves from a first position area to a second position area, the second end 52 of the indicator 5 further moves the slider 42 from the first section to the second section of the sliding slot 41. In this embodiment, the second direction is the clockwise direction shown in the figure, but the present disclosure is not limited to this configuration. A window is provided on the stapler body portion corresponding to the first position area and the second position area, for the purpose of observing the position of the first end 51 of the indicator during use. When the first end 51 of the indicator 5 is in the first position area, the handle assembly is in the insurance state thus the stapler cannot be fired. When the first end 51 of the indicator 5 is in the second position area, the stapler can be fired. In order to cue the operator that the stapler is in ready to be fired, the second position area is marked in green, which has been disclosed in the prior art.

Furthermore, a pressure spring 45 is further disposed to the slider 42 to reset the slider 42 after departing from the indicator 5. When the first end 51 of the indicator 5 moves from the first position area towards the second position area, the second end 52 of the indicator 5 advances the slider 42 from the first section to the second section of the sliding slot 41, compressing and deforming the pressure spring 45. When the first end 51 of the indicator 5 returns to the first position area, the restoring force of the pressure spring 45 then biases the slider 42 back to the first section of the sliding slot 41. Two side walls of the first cavity 13 are respectively provided with a sliding slot 41, and the slider 42 includes two sliding portions 421 and an abutment between the two sliding portions 422. Each sliding portion 421 is slidably disposed in the sliding slot 41. The pressure spring 45 is provided between each sliding slot 41 and the corresponding sliding portion 421, respectively.

In the embodiment of the present disclosure, a first pivot pin 31 passes through both the first handle 1 and the second handle 2. The first pivot pin 31 is fixedly secured to a housing 74 of the stapler, and a first torsion spring 32 is sleeved thereon. Both ends of the first torsion spring 32 are respectively attached to the housing 74 of the stapler and the second handle 2. As an external force is released after rotation, the second handle 2 is biased by the first torsion spring and reset to the initial position.

Since both the first handle 1 and the second handle 2 are both rotated around the first pivot pin 31, the operator's experience is improved. Additionally, in the embodiment, a second torsion spring 34 and a second pivot pin 33 are further provided for resetting the first handle 1. The second pivot pin 33 is fixedly secured to the housing 74 of the stapler, the second torsion spring 34 is sleeved on the second pivot pin 33, and two ends of the second torsion spring 34 are respectively attached to the housing 74 of the stapler and the first handle 1.

The first handle 1 and the second handle 2 are pivotally attached to the housing of the stapler. The second torsion spring 34 merely applies a resistance to the first handle 1 in the counterclockwise rotation, not in the clockwise rotation. If the initial position of the first handle 1 is not limited, the angular deflection of the first handle 1 with respect to the housing of the stapler 74 may be too great to render a stable structure of the handle assembly.

Figure 3:
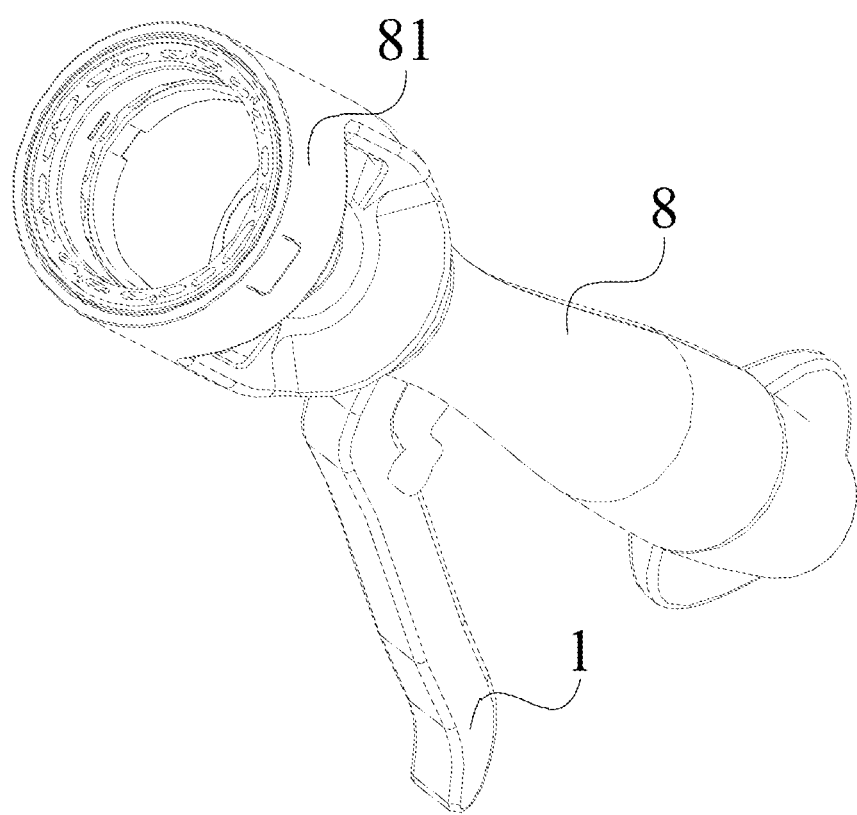
FIG. 3 is a schematic view of the handle assembly according to the embodiment of the present disclosure applied in a circumcision stapler.
Figure 4:
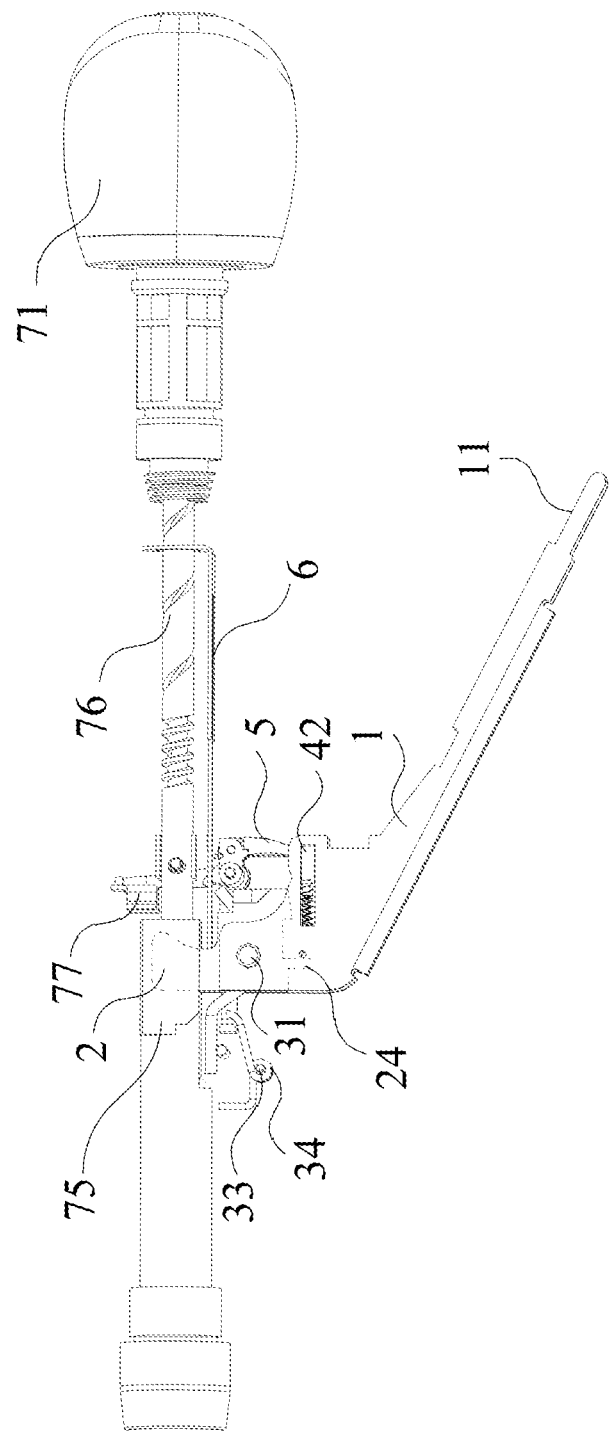
FIG. 4 is a schematic view according to the embodiment of the present disclosure when the handle assembly is in an initial state.

The present disclosure can be applied not only to a conventional circular stapler, but also to a circumcision stapler. For example, FIG. 3 shows the structure of a body portion 8 of the circumcision stapler. A distal end of the circumcision stapler body portion 8 includes a cartridge assembly 81, and a glans cap assembly (not shown in the figure) cooperated with the cartridge assembly 81. In using the circumcision stapler, the second handle 2 is movably connected to one end of the circumcision stapler. The second end of the second handle 2 is configured to push a staple pushing component when the stapler is ready to be fired, to fire the circumcision stapler.

Figure 5:
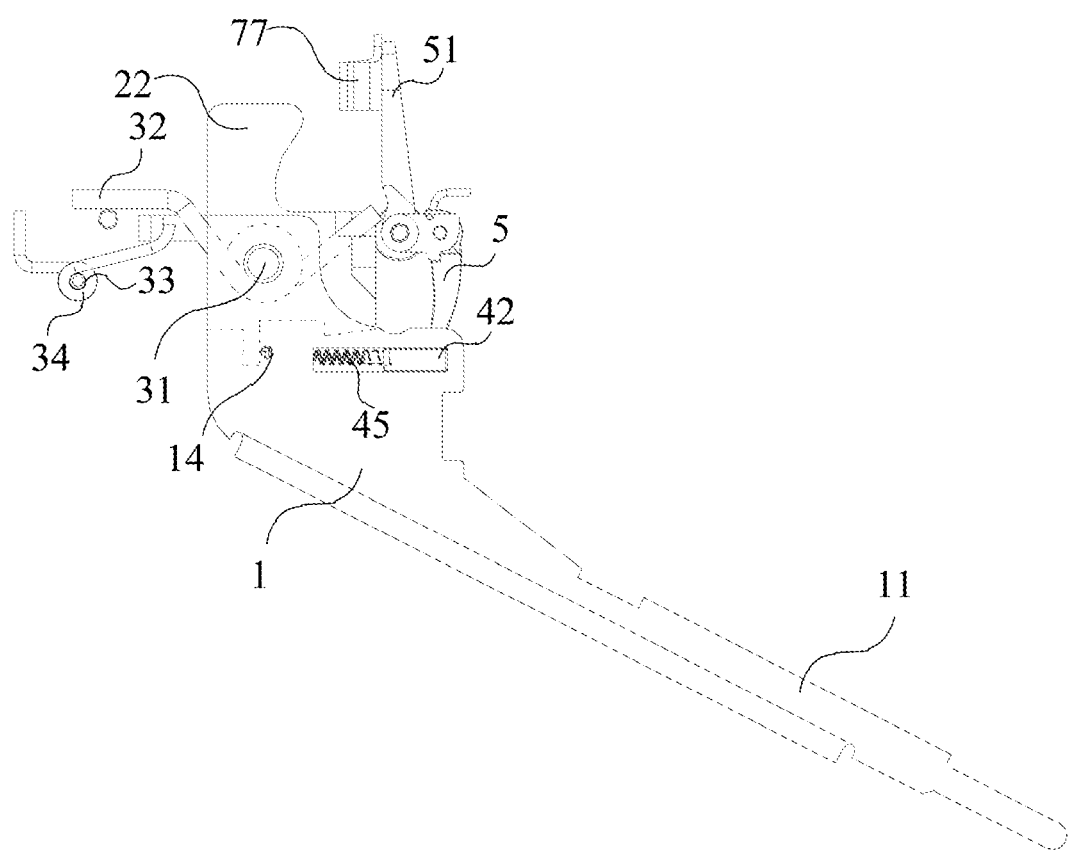
FIG. 5 is a schematic view according to the embodiment of the present disclosure when the handle assembly is in an initial state.
Figure 6:
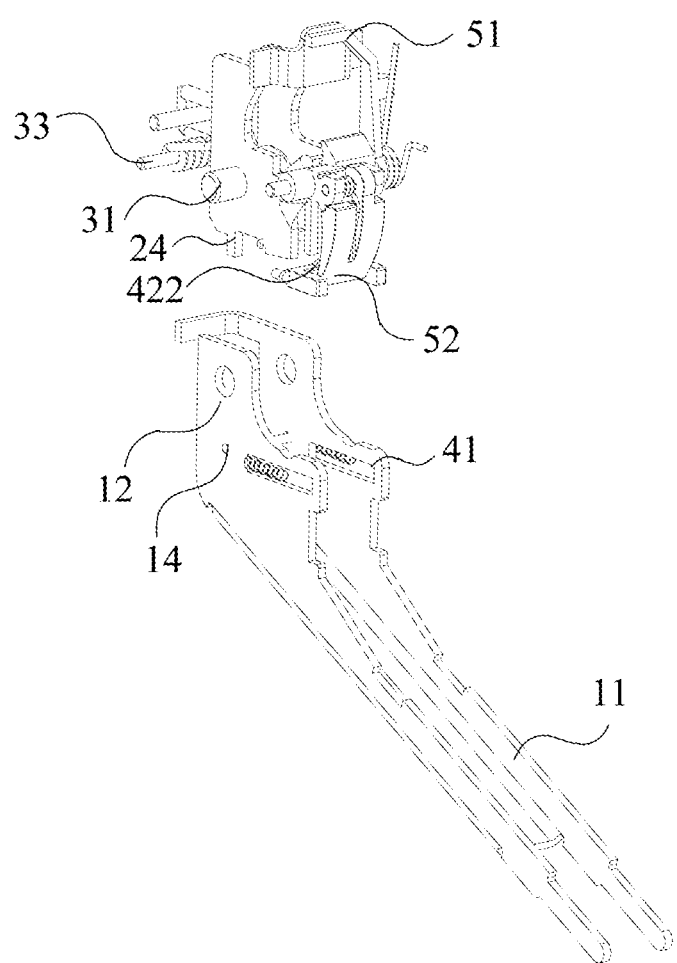
FIG. 6 is a schematic view according to the embodiment of the present disclosure when the handle assembly is in an initial state.
Figure 7:
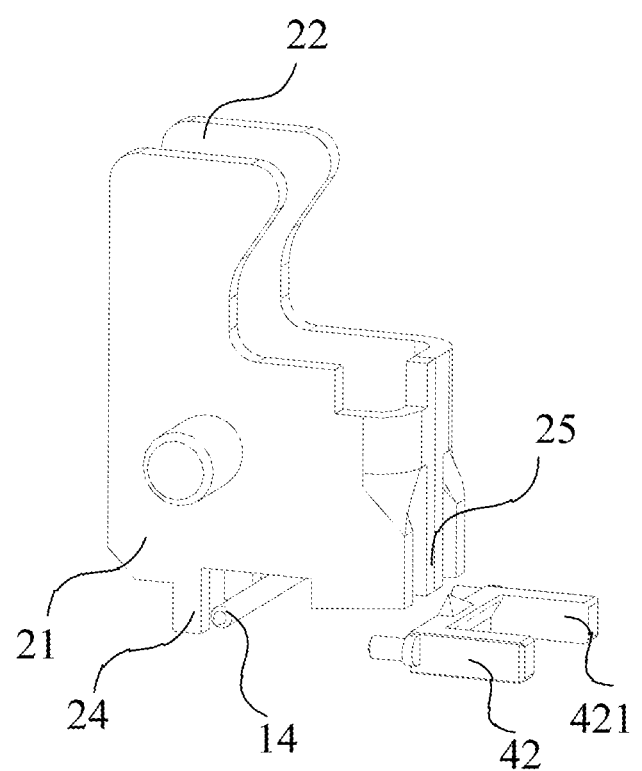
FIG. 7 is a schematic view of a second handle in relation to a slider according to the embodiment of the present disclosure when the handle assembly is in the initial state.
Figure 8:
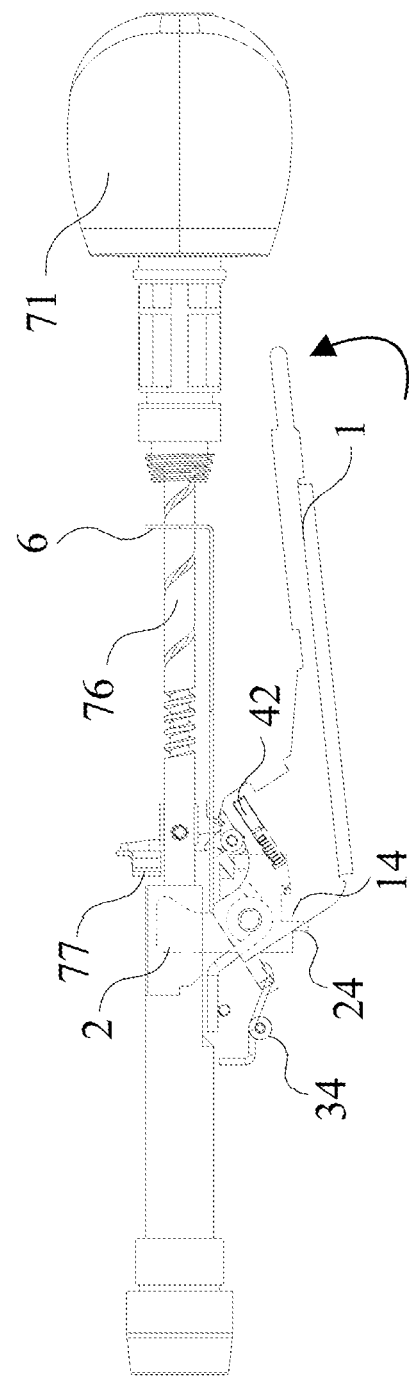
FIG. 8 is a schematic view according to the embodiment of the present disclosure when the handle assembly is in an invalid state.

Therefore, as shown in FIGS. 5-7, in the present disclosure, a first limit portion and a second limit portion that limit the clockwise rotation of the first handle 1 are further provided to the first handle 1 and the second handle 2, respectively. In this embodiment, the first handle 1 includes a first cavity. Inside the first cavity, a limit pivot pin 14 is provided as the first limit portion. Both ends of the limit pivot pin 14 are fixed to two side walls of the first cavity, respectively. The second handle 2 includes a second cavity. A handle limit portion 24 protruding from a lower part of each side wall of the second cavity is provided as a second limit portion. An imaginary line connecting the two handle limit portions 24 is parallel to a central axis of the limit pivot pin 14. When the first handle 1 is in the initial position, the limit pivot pin 14 simultaneously abuts the two handle limit portions 24. Since the limit pivot pin 14 is provided on a proximal end side of the handle limit portion 24, it prevents clockwise rotation of the first handle 1, and limits an initial opening angle of the first handle. However, it has no effect in counterclockwise rotation of the first handle.

The handle limit portion 24 could either be a limit post integrally formed with the side walls of the second handle 2 or a separate limit post that is fixed to the second handle 2 by welding or fasteners. Similarly, both ends of the limit pivot pin 14 can also be fixed to the side walls of the first handle 1 by welding or fasteners.

In addition, by having the structural design of the limit pivot pin 14 and the handle limit portion 24, the initial position of the second handle 2 is also limited. The second handle 2 can only be rotated clockwise with respect to the first handle 1, but not counterclockwise. Therefore, in the invalid state, the first handle 1 can be rotated counterclockwise with respect to the second handle 2. In a firing state, the first handle 1 and the second handle 2 can be rotated simultaneously in the counterclockwise direction. However, when the first handle 1 is not rotated, the second handle 2 cannot be rotated counterclockwise to fire the stapler, further ensuring safety in use.

This embodiment provides one way to implement the first limit portion of the first handle 1 and the second limit portion of the second handle 2. The first limit portion may be formed in a square column shape or other shapes that are not limited to the structure of the limit pivot pin 14. Alternatively, the first limit portion may be formed by two limit plates, disposed respectively on the inner surface of the side walls of the first cavity. The second limit portion may not be limited to the structure of the two handle limit portion 24, alternatives such as an integral limit column or a limit pivot pin, or two limit plates provided on the outer surface of the side walls of the second cavity can be used, all of which fall within the scope of the present disclosure.

The mechanical structure in connecting the first handle 1 and the second handle 2 provided in the present disclosure is non-limiting. All other alternative structures fall within the scope of the present disclosure. For instance, the second torsion spring and the second limit pivot pin used for resetting the first handle could be replaced by at least one pressure spring. The pressure spring or springs are attached between the first handle and the housing of the stapler. When the first handle is rotated, the pressure spring is compressed and deformed; when released, the first handle is biased by the pressure spring to return to the initial position. Furthermore, a double-rotation-center structure is available. Similarly, a first and a second torsion spring and a first and a second limit pivot pin are used. The first pivot pin is fixedly secured to the second handle and passes through the first handle. The first torsion spring is sleeved on the first torsion spring. Two ends of the first torsion spring abut the first handle and the second handle respectively. As such, the first handle can be reset. The second limit pivot pin is fixedly secured to the housing of the stapler and passes through the second handle. The second torsion spring is sleeved on the second limit pivot pin. Two ends of the second torsion spring abut the second handle and the housing of the stapler, respectively. As such, the second handle can be reset. The first handle and the second handle are rotated around the first torsion spring and the second torsion spring, respectively.

In addition, this embodiment only provides one implementation to control the linkage state of the first handle 1 and the second handle 2. But the disclosure is not limited thereto. In other embodiments, for example, the sliding slot and the slider can be provided on the second handle. When the first handle and the second handle are not linked, the slider does not engage the first handle. When the first handle and the second handle are linked, the slider engages the second handle. Alternatively, an elastic member could be provided between the first handle and the second handle. When the elastic member expands, the first handle and the second handle are linked together. In some embodiments using a slider, the way to change the slider position is not limited to the abovementioned methods. Other means for moving the slider in the sliding slot such as pushing, pulling, attracting, or repelling all fall within the scope of the present disclosure.

FIGS. 8 to 11 show the structure of the handle assembly according to the embodiment in the invalid state. In this state, the pulling sheet 6 does not pull the indicator 5, so the position of the indicator 5 is unchanged. The slider 42 is still positioned in the first section of the sliding slot 41. On its rotational path, the slider 42 does not engage the handle abutment 25 of the second handle 2. It should be noted that, in the initial state, the slider 42 is positioned by the slider resetting pressure spring 45 at the end of the first section of the sliding slot 41 far from the second section, i.e. the right end of the first section shown in the figure. Alternatively, the initial position of the slider 42 may be limited by a second end 52 of the indicator 5. In this embodiment, a first end 11 of the first handle 1 is a gripping portion, and a second end 12 includes an attachment portion; a first end 21 of the second handle 2 is positioned inside the cavity of the attachment portion, and a second end 22 engages the staple pushing rod 75. As such, the stapler is in an insurance state. Since the torsion force of the second torsion spring 34 is much smaller compared to the force required for firing the stapler, the first handle 1 can be rotated counterclockwise around the first pivot pin 31 with a very small force, and the second handle 2 continues to enter inside the cavity of the first handle 1. As the first handle 1 and the second handle 2 are not linked, when the first handle 1 is forced to rotate, it does not rotate the second handle 2 thus the firing of the stapler cannot be completed. The stapler provides a tactile feedback that the first end 51 of the indicator 5 has not reached the second position area and the stapler has not been fired. When the external force is released, the first handle 1 is reset by the second torsion spring 34.

Figure 9:
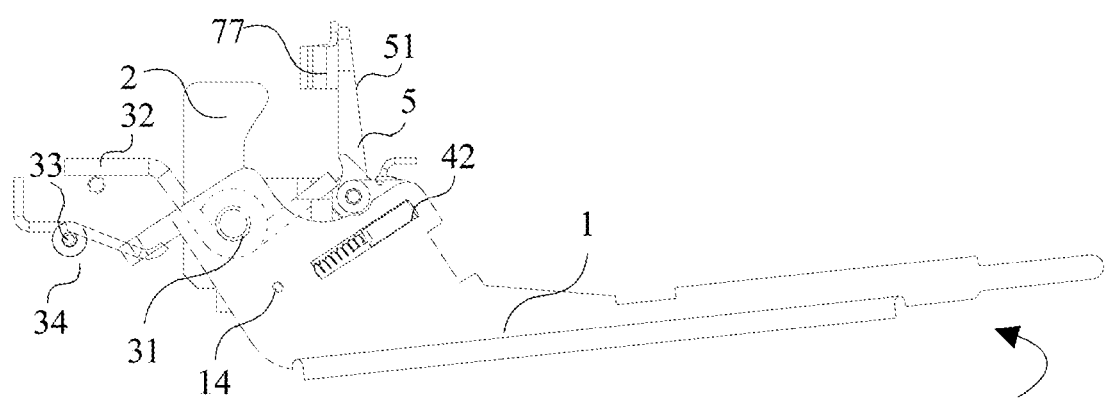
FIG. 9 is a schematic view according to the embodiment of the present disclosure when the handle assembly is in an invalid state.
Figure 10:
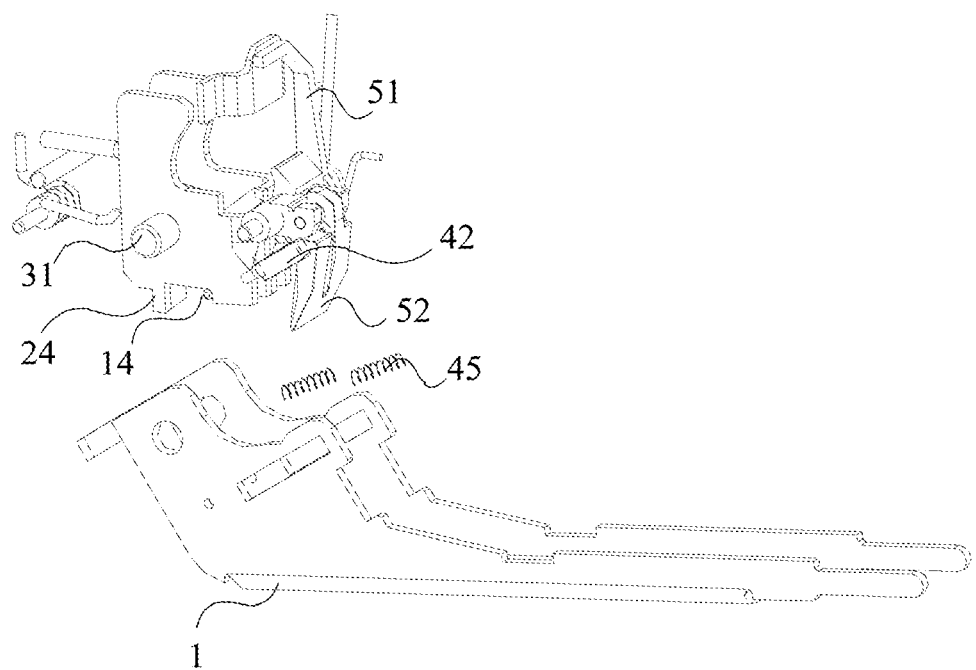
FIG. 10 is a schematic view according to the embodiment of the present disclosure when the handle assembly is in an invalid state.
Figure 11:
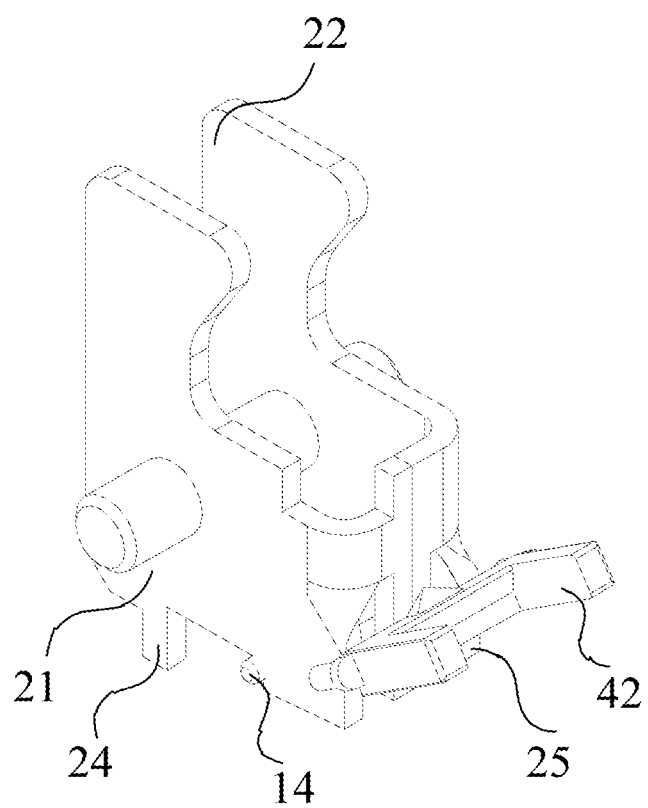
FIG. 11 is a schematic view of the second handle in relation to the slider according to the embodiment of the present disclosure when the handle assembly is in the invalid state.
Figure 12:
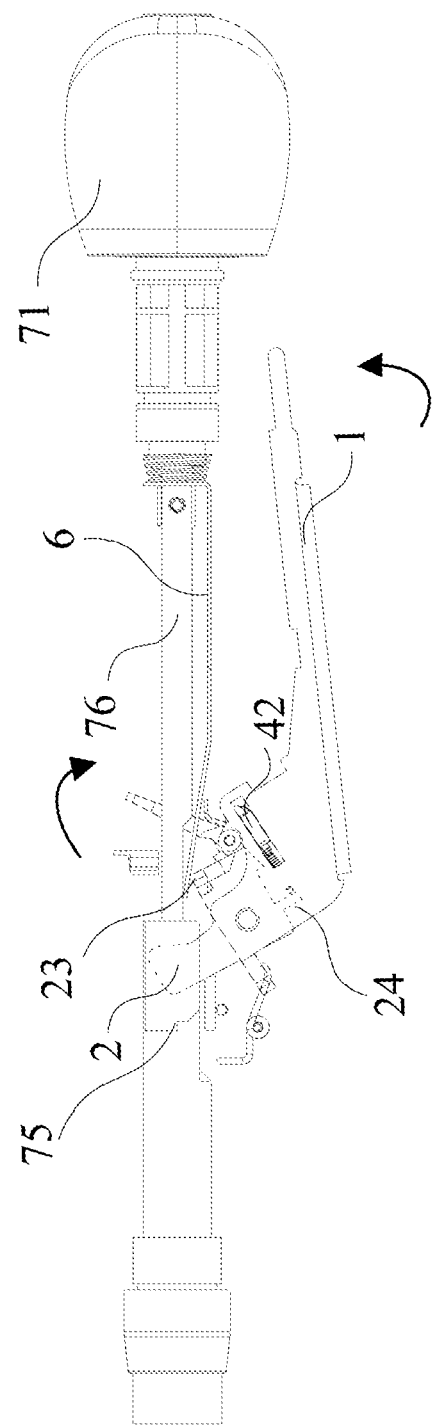
FIG. 12 is a schematic view according to the embodiment of the present disclosure when the handle assembly is in a firing state.
Figure 13:
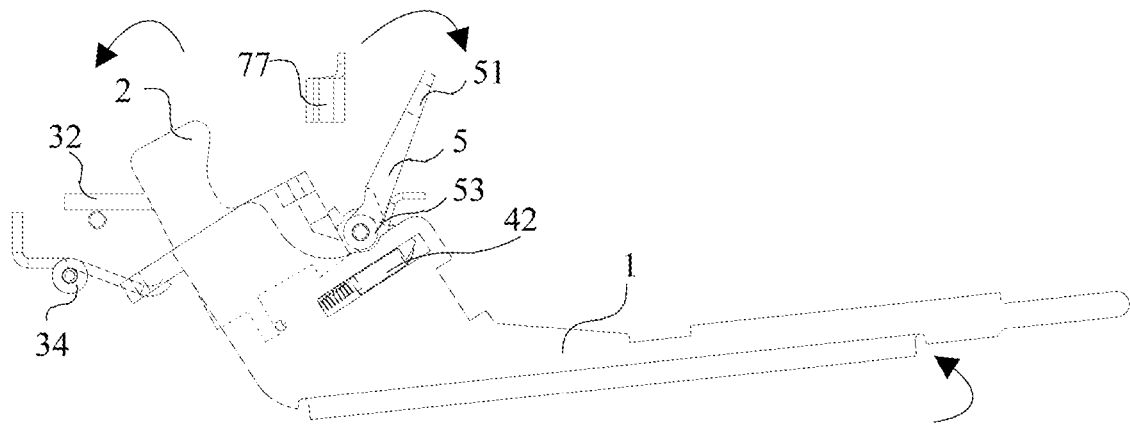
FIG. 13 is a schematic view according to the embodiment of the present disclosure when the handle assembly is in a firing state.
Figure 14:
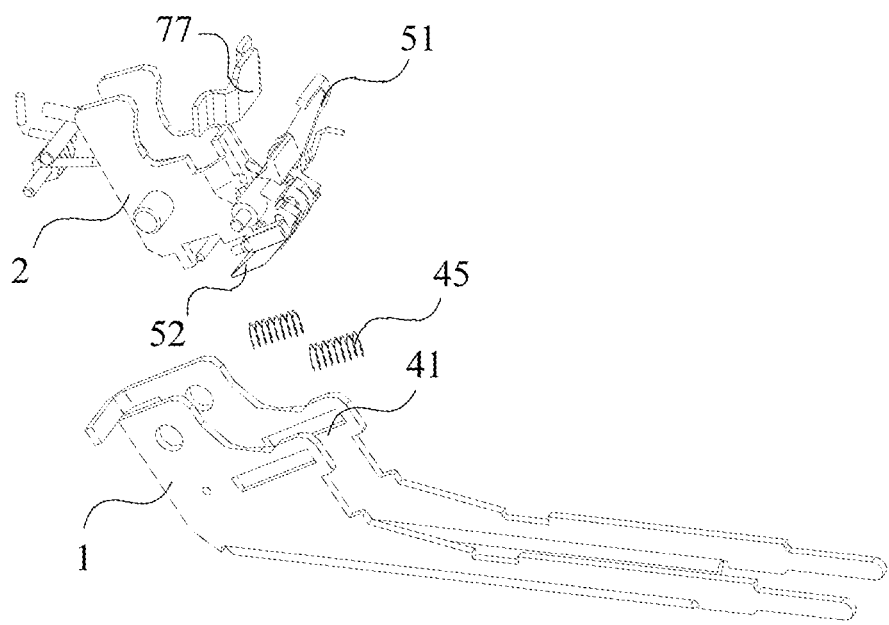
FIG. 14 is a schematic view according to the embodiment of the present disclosure when the handle assembly is in a firing state.
Figure 15:
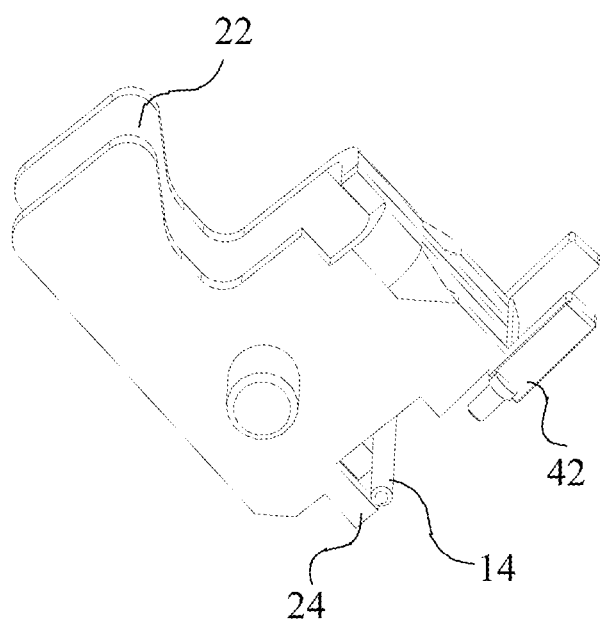
FIG. 15 is a schematic view of the second handle in relation to the slider, according to the embodiment of the present disclosure, when the handle assembly is in the firing state.

As shown in FIG. 9, since the first handle 1 is rotated counterclockwise, the handle limit portion 24 and the limit pivot pin 14 are disengaged, thus the handle limit portion 24 and the limit pivot pin 14 no longer limit the position of the first handle 1.

FIGS. 12 to 15 show the structure of the handle assembly according to the embodiment of the present disclosure in the firing state. In this process, rotating the knob 71 causes the screw rod 76 to effect advancement of the pulling sheet 6 proximally, thereby rotating the first end 51 of the indicator 5 clockwise to move from the first position area to the second position area. The second end 52 of the indicator 5 pushes the slider 42 toward the second section 412 of the slide slot 41. When the first handle 1 is squeezed and rotated counterclockwise, the slider 42 engages the handle abutment 25 and prevents the second handle 2 from continuing to enter the internal cavity of the first handle 1. As such, the second handle 2 and the first handle 1 become linked. The second handle 2 is rotated counterclockwise in synchronization with the first handle 1, and a second end 22 of the second handle 2 pushes the staple pushing rod 75 which further pushes a staple pushing sheet and a circular cutter of the stapler in performing suturing and cutting operations.

As shown in the figures, the slider resetting pressure spring 45 is being compressed during the movement of the slider 42. When the stapler is fired, the pulling sheet 6 is ejected by a pulling sheet abutment 23 at an ejection point, so that the hook 61 of the pulling sheet 6 is disengaged from the indicator 5. The indicator 5 will automatically return to the initial position. In this embodiment, a metal sheet 77 is provided in the housing 74 of the stapler at a position corresponding to the first end 51 of the indicator 5, and when the indicator 5 returns to its initial position, it will engage the metal sheet 77, making a clicking sound cueing the operator that the indicator 5 has been reset. Since the first end 51 of the indicator 5 returns to the first position area, the second end 52 of the indicator 5 is disengaged from the slider 42. The slider 42 is then biased to the first section of the sliding slot 41 by the slider resetting pressure spring 45 until the reset is complete. The second handle 2 is reset by the bias of the first torsion spring 32. As the first handle 1 is engaged with the second handle 2 due to the slider, the first handle 1 is firstly reset along with the second handle 2, and then reset by the second torsion spring 34.

In the firing state, as the first handle 1 and the second handle 2 are rotated simultaneously, their relative position is unchanged. Therefore the limit pivot pin 14 remains in engagement with the handle limit portion 24. As the first handle 1 is released and rotated towards its initial position, it rotates the second handle 2. The first handle 1 and the second handle 2 are rotated simultaneously which speeds up the reset.

An embodiment of the present disclosure further provides a stapler, including the abovementioned handle assembly. When the stapler is not ready to be fired, the first handle is not engaged with the second handle, and the stapler is not fired. The operator can also identify the firing state from the operating experience. Only when the stapler is ready to be fired, the first handle engages the second handle and can fire the stapler. In addition to avoiding the accidental firing of the stapler, rupture in the stapler housing is avoided too. This embodiment is provided with an angle limit structure located between the housing of the stapler and the first handle, limiting the initial position and the reset position of the first handle, thus ensuring the structural stability of the stapler.

The handle assembly and the stapler including the handle assembly provided by the present disclosure have the following advantages:

The present disclosure provides a handle assembly and a stapler including the handle assembly. The handle assembly includes a first handle and a second handle which can be configured in different linkage states, and only the rotation of the second handle can fire the stapler, thereby avoiding accidental firing. In the invalid state, the first handle can still be squeezed without causing rupture of the housing. The first handle is provided with the first limit portion and the second handle is provided with the second limit portion. In the initial state, the two limit portions abut each other to prevent the rotation of the first handle in the second direction, so that the angular deflection of the first handle in its initial position will not be too great, ensuring high accuracy of the initial position of the first handle and improving the operator's experience; in addition, the two limit portions limit the initial position of the second handle, so that when the first handle is not rotated, the second handle cannot be rotated to fire the stapler.

The detailed description of the present disclosure with reference to specific selected embodiments hereof should not be construed as limiting, but merely as exemplifications of the present disclosure. Those skilled in the art will envision other modifications within the scope and spirit of the claims appended hereto.

What is claimed is:

1. A handle assembly for firing a stapler, comprising a first handle and a second handle, wherein one end of the first handle is rotatably attached to one end of the second handle; when the first and the second handle are not linked, the second handle is in an insurance position; when the first handle and the second handle are linked, the rotation of the first handle in a first direction moves the second handle from the insurance position to a firing position;

the first handle is provided, on its one end, with a first limit portion, and the second handle is provided, on its one end, with a second limit portion; the first limit portion is located on a proximal end side of the second limit portion; when the first handle is in an initial position, the second limit portion engages the first limit portion to block rotation of the first handle in a second direction.

2. The handle assembly according to claim 1, wherein the first direction is counterclockwise, and the second direction is clockwise; or, the first direction is clockwise, the second direction is counterclockwise.

3. The handle assembly according to claim 1, wherein the first handle comprises a first cavity, the first limit portion is a limit pivot pin located inside the first cavity, and two ends of the limit pivot pin are fixed to two side walls of the first cavity respectively;

when the first handle is in the initial position, a side surface of the limit pivot pin abuts the second limit portion.

4. The handle assembly according to claim 3, wherein the second limit portion comprises two limit posts, with an imaginary line connecting thereto parallel to a central axis of the limit pivot pin;

when the first handle is in the initial position, the limit pivot pin simultaneously abuts both limit posts.

5. The handle assembly according to claim 1, wherein the second handle is provided with a second cavity, and the second limit portion comprises two limit posts which are respectively located on lower parts of side walls of the second cavity;

when the first handle is in the initial position, the first limit portion simultaneously abuts both limit posts.

6. The handle assembly according to claim 5, wherein the limit posts and the side walls of the second cavity are integrally formed.

7. The handle assembly according to claim 1, wherein the first handle is provided with a sliding slot comprising a first section and a second section connected with each other; a slider is slidably disposed in the sliding slot;

when the slider is located in the first section of the sliding slot, as the first handle is rotated in the first direction, the slider does not engage the second handle, thus the first handle and the second handle are not linked; when the slider is located in the second section of the sliding slot, as the first handle is rotated in the first direction, the slider abuts the second handle and pushes the second handle to rotate with the first handle.

8. The handle assembly according to claim 7, further comprising an indicator attached to a distal end of a pulling sheet, a proximal end of the pulling sheet is sleeved on a screw rod; a knob provided at a distal end of the screw rod, and when the knob is rotated, the pulling sheet is moved thereby towards a proximal end of the stapler; the pulling sheet moves the indicator from a first position area to a second position area, while pushing the slider from the first section to the second section of the sliding slot.

9. The handle assembly according to claim 1, further comprising:
a first pivot pin, passing through the first handle and the second handle and fixed to a housing of the stapler;
a first torsion spring sleeved on the first pivot pin, and two ends thereof abutting the housing of the stapler and the second handle, respectively;
a second pivot pin fixed to the housing of the stapler;
a second torsion spring sleeved on the second pivot pin, and two ends of the second torsion spring respectively abut the housing of the stapler and the first handle.

10. A stapler comprising the handle assembly according to claim 1.

* * * * *